United States Patent [19]

Moder

[11] Patent Number: 5,457,206

[45] Date of Patent: Oct. 10, 1995

[54] PROCESS FOR PREPARING INTERMEDIATES TO NIZATIDINE AND RELATED COMPOUNDS

[75] Inventor: Kenneth P. Moder, West Lafayette, Ind.

[73] Assignee: Eli Lilly and Company, Indianapolis, Ind.

[21] Appl. No.: 269,597

[22] Filed: Jul. 1, 1994

Related U.S. Application Data

[62] Division of Ser. No. 76,489, Jun. 14, 1993, Pat. No. 5,334,725, which is a continuation of Ser. No. 952,426, Sep. 28, 1992, abandoned, which is a division of Ser. No. 703,526, May 21, 1991, abandoned.

[51] Int. Cl.$^6$ ............... C07D 277/28; C07D 513/10
[52] U.S. Cl. ............ 548/205; 548/147; 548/189; 544/70; 544/137; 546/15; 546/209
[58] Field of Search ............... 548/203, 205, 548/364.1, 182, 189, 186

[56] References Cited

U.S. PATENT DOCUMENTS 4,904,792  2/1990  Ploch .................... 548/205

FOREIGN PATENT DOCUMENTS 46-20702  10/1971  Japan ................... 548/147
90-07511   7/1990  WIPO .................... 548/147

OTHER PUBLICATIONS

Brown et al., *Tet. Let.*, 32, 2797–2798 (1969).
Silburg et al., *Chem. Ber.*, 94, 2887–2894 (1961).

*Primary Examiner*—Floyd D. Higel
*Attorney, Agent, or Firm*—MaCharri Vorndran-Jones; Douglas J. Taylor

[57] ABSTRACT

The present invention provides a process for preparing a 2-(aminomethyl)-4-thiazolemethanol. The compounds produced by the process of the present invention are useful for synthesizing anti-ulcer compounds such as Nizatidine.

12 Claims, No Drawings

PROCESS FOR PREPARING INTERMEDIATES TO NIZATIDINE AND RELATED COMPOUNDS

This application is a division of application Ser. No. 08/076,489, filed on Jun. 14, 1993, now issued U.S. Pat. No. 5,334,725 which is a continuation of application Ser. No. 07/952,426, filed on Sep. 28, 1992, now abandoned, which is a division of application Ser. No. 07/703,526, filed on May 21, 1991, now abandoned.

BACKGROUND OF THE INVENTION

U.S. Pat. No. 4,904,792 teaches that Nizatidine, N-[2-[[ [2-[(dimethylamino)methyl]-4-thiazolyl]methyl]thio]ethyl]-N'-methyl-2-nitro-1,1-ethenediamine, and related compounds of the general formula

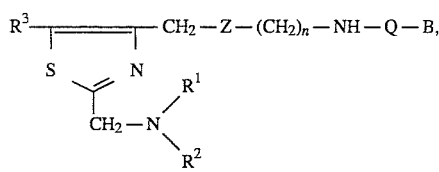

wherein $R^1$ is hydrogen, methyl, ethyl, benzyl or benzoyl; $R^2$ is methyl or ethyl; or $R^1$ and $R^2$, taken together with the nitrogen atom to which they are attached, form a pyrrolidine, piperidene or morpholine ring;

$R^3$ is hydrogen or methyl;

Z is —O— or —S—;

n is 2 or 3;

Q is

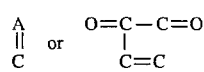

wherein A is N—CN, N—NO$_2$, CH—NO$_2$, S, N—SO$_2$-aryl, N—SO$_2$-methyl or N—CO—NH$_2$ (where aryl is tolyl or phenyl); and B is NHR, where R is methyl, ethyl, (2-hydroxy)ethyl or cyclopropyl, or YR$^4$ where Y is —O— or —S— and R4 is $C_1$–$C_3$ alkyl, —CH$_2$—($C_2$–$C_4$ alkenyl) or benzyl, are particularly effective H$_2$-receptor antagonists, or are useful as intermediates in the preparation of such pharmaceutically active compounds. As such, the patent compounds are useful as anti-ulcer agents capable of inhibiting gastric acid secretion in mammals. Nizatidine, in particular, is an effective anti-ulcer drug currently sold under the trademark AXID.

U.S. Pat. No. 4,904,792 discloses Nizatidine, and the other related compounds set forth in the patent, are synthesized using a multi-step process. The first step of this process comprises reacting an acid addition salt of an aminomethylthioacetamide with a beta-bromo-alpha-ketoester, such as ethyl bromopyruvate, so as to provide an alkyl-2-(aminomethyl)-4-thiazolecarboxylate. Reduction of such compound with a suitable hydride reducing agent yields a 2-(aminomethyl)-4-thiazolemethanol compound, which is then converted to a [2-(aminomethyl)-4-thiazolylmethylthio]alkylamine by reaction with cysteamine or 3-mercaptopropylamine in the presence of an acid. Such alkylamine is then readily converted to the pharmaceutically active compounds of the patent via several different reaction pathways.

The process disclosed in U.S. Pat. No. 4,904,792 has several disadvantages which limit its utility on a production scale setting. Firstly, several of the reactants required by the patent's process are rather expensive. Secondly, the process yield, on a production scale, is less than desirable. Finally, the purity of the final product (which is directly related to the purity of the alkylamine intermediate), when prepared on a production scale utilizing the procedure described above, is inconsistent and sometimes insufficient. When product of insufficient purity is obtained, such product must be recrystallized in order to increase purity to an acceptable level. Such recrystallization results in product loss thereby lowering process yield even further. All of these factors, when combined, render the process disclosed in U.S. Pat. No. 4,904,792 suitable for preparing laboratory scale quantities of product, but less than desirable for preparing production scale quantities of same.

Accordingly, an object of the present invention is to provide a process for preparing Nizatidine, and related compounds, which is eminently suitable for use in a production scale setting. The process of the present invention utilizes relatively inexpensive substrates to prepare the key alkylamine intermediate of U.S. Pat. No. 4,904,792. Furthermore, such key intermediate can be prepared in both high yield and purity. As such, the process of the present invention is believed to provide a more economical synthesis for particularly useful anti-ulcer agents than previously known routes for preparing such compounds.

SUMMARY OF THE INVENTION

The present invention provides a novel process for preparing a 2-(aminomethyl)-4-thiazolemethanol having the formula

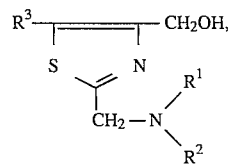

wherein $R^1$ is hydrogen, methyl, ethyl, benzyl or benzoyl; $R^2$ is methyl or ethyl; or $R^1$ and $R^2$, taken together with the nitrogen atom to which they are attached, form a pyrrolidine, piperidine or morpholine ring; and $R^3$ is hydrogen or methyl, which comprises reacting a 4-hydroxy-4-chloromethyl-2-(aminomethyl)thiazoline of the formula

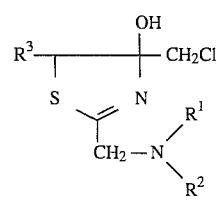

with an alkali metal base in an inert solvent. The thiazolemethanol product produced by the process of the present invention is then readily converted to a [2-(aminomethyl)-4-thiazolylmethylthio]alkylamine, and ultimately to nizatidine or one of its related compounds as set forth in U.S. Pat.

No. 4,904,792, using the procedures described in that patent.

DETAILED DESCRIPTION OF THE INVENTION

The process of the present invention reacts a 4-hydroxy-4-chloromethyl-2-(aminomethyl)thiazoline of the formula

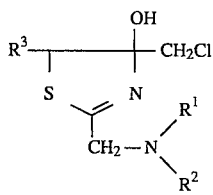

with an alkali metal base in an inert solvent so as to provide a 2-(aminomethyl)-4-thiazolemethanol of the formula

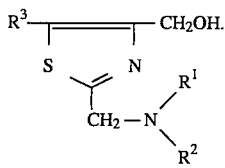

Solvent choice for the process described above is not critical so long as the reactants are sufficiently solubilized to effect the desired reaction and the solvent is inert to the reaction conditions employed. Preferred inert solvents for use in the process of the present invention are the alcohol solvents, especially methanol, and the aromatic solvents, especially toluene. Toluene is the most preferred solvent for use in the present process.

Any number of conventional organic or inorganic alkali metal bases may be employed in the process of the present invention. Typical organic bases which may be employed include the alkali metal alkoxides such as sodium methoxide, potassium t-butoxide, sodium ethoxide, potassium methoxide and the like. Typical inorganic bases which may be employed include the alkali metal hydroxides such as sodium hydroxide, potassium hydroxide, lithium hydroxide and the like. The alkali metals themselves, such as sodium, potassium and the like, and the alkali metal hydrides such as lithium hydride, sodium hydride and the like, may also be employed as bases in the present process as well. The carbonate inorganic bases, such as sodium bicarbonate and potassium carbonate, however, do not appear to be suitable for use in the process of the present invention.

While the process of the present invention can employ any of the bases discussed above, potassium hydroxide provides a particularly preferred base for meeting the object of the present invention. Potassium hydroxide is inexpensive. Potassium hydroxide also allows synthesis of the 2-(aminomethyl)-4-thiazolemethanol product is converted into the key alkylamine intermediate of U.S. Pat. No. 4,904,792, the use of potassium hydroxide in the present process plays a crucial role in providing an economical method of synthesizing Nizatidine and its related compounds in high yield and purity. Accordingly, potassium hydroxide is a particularly preferred base for use in the process of the present invention.

The amount of base required in the process of the present invention is also not crucial. In general, at least an equimolar amount of base, or a slight excess thereof, relative to the 4-hydroxy-4-chloromethyl-2-(aminomethyl) thiazoline substrate is employed in order to ensure that complete reaction of the thiazoline substrate is obtained. However, excess base, for example up to 5 equivalents of base relative to the thiazoline substrate, may also be employed without deleteriously affecting the desired reaction. A preferred base/thiazoline substrate ratio ranges from about 1.3 equivalents of base to about 2.8 equivalents of base, with 1.3 equivalents of base relative to the thiazoline substrate being the most preferred base/thiazoline ratio.

As the base reacts with the thiazoline substrate of the present invention such substrate is converted to a 2-(aminomethyl)-4-exomethylene-thiazoline epoxide of the formula

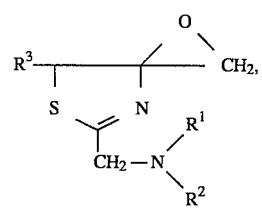

a salt (such as potassium chloride) and water. This epoxide intermediate then rearranges in-situ to provide the desired 2-(aminomethyl)-4-thiazolemethanol product of the process of the present invention.

The salt produced by the reaction described above accumulates as the reaction proceeds. Depending on the type and amount of inert solvent employed, and the solubility of the salt in such solvent, salt precipitation may occur before the process of the present invention is complete. To prevent salt precipitation, water may be added to the reaction mixture in a quantity sufficient to keep the salt in solution. Water addition may be accomplished by adding water directly, by adding water in the form of an aqueous basic solution (for example an aqueous potassium hydroxide solution) or a combination of both. Water addition is not required by the process of the present invention and is only utilized if prevention of salt precipitation is desired. Due to the explosive nature of certain of the bases which may be employed in the process of the present invention, for example sodium metal, in some cases water addition should be avoided.

The concentration of thiazoline substrate and base in the inert solvent is not critical. In general, it is desirable to use as concentrated a solution as possible in order to minimize any product loss which might occur during product isolation. However, sufficient solvent should be employed in order to ensure that all reactants and reaction products (with the possible exception of the salt) stay in solution until reaction is complete.

The process of the present invention is generally conducted at a temperature in the range of from about 0° C. to about 60° C. When conducted at a temperature in such range, the process of the present invention is generally substantially complete after about 15 minutes to about 8 hours. Once the reaction is substantially complete, the 2-(aminomethyl)-4-thiazolemethanol compounds prepared by the process of the present invention can be isolated using standard isolation techniques such as extraction or distillation. Purification of the isolated compound may be accomplished using standard techniques such as high vacuum distillation, if desired.

The 2-(aminomethyl)-4-thiazolemethanol compounds prepared according to the instant process are then readily converted to the key [2-(aminomethyl)-4-thiazolylmethylthio]alkylamine intermediate of U.S. Pat. No. 4,904,792 using procedures detailed in that patent. The alkylamine intermediate can then, in turn, be converted to a pharmaceutically active agent, such as Nizatidine, by utilizing procedures set forth in U.S. Pat. No. 4,904,792.

As noted above, the process of the present invention employs a 4-hydroxy-4-chloromethyl-2-(aminomethyl) thiazoline starting material. Such substrate is readily prepared from compounds which are either commercially available, or easily prepared from compounds which are commercially available, according to the following reaction procedure

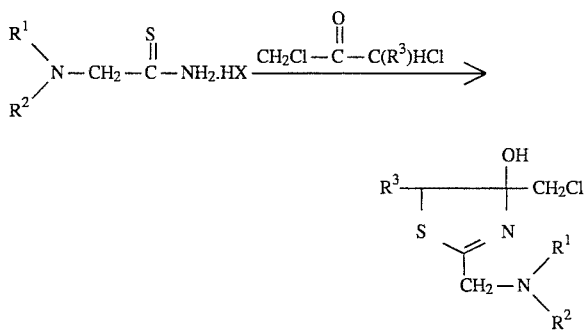

In the above procedure $R^1$, $R^2$ and $R^3$ are as defined previously and X is a halogen atom.

In the above reaction, an acid addition salt of an aminoalkylthioacetamide is reacted with a slight excess (about 1.2 equivalents) of a 1,3-dichloroketone so as to provide the 4-hydroxy-4-chloromethyl-2-(aminomethyl) thiazoline starting material of the process of the present invention. The reaction is generally conducted in an inert solvent such as methylene chloride or toluene. Furthermore, at least two equivalents of an acid scavenger, such as sodium bicarbonate, should be employed in order to optimize reaction yield. The reaction should further be conducted at a temperature in the range of from 20° C. to 70° C., with 40° C. to 60° C. being an optimal temperature range. When conducted at a temperature in the range of from 20° C. to 60° C. the reaction will generally be substantially complete after about 1 hour to about 24 hours. Once complete, the 4-hydroxy-4-chloromethyl-2-(aminomethyl)thiazoline may be isolated, if desired, using standard isolation procedures. However, since the thiazoline compound is unstable and poses a severe health hazard, isolation of such compound is generally not preferred.

To obviate the instability and health problems posed by the thiazoline compound such compound is preferably left in solution. This solution may be readily employed in the process of the present invention once the acid salts produced by the process for preparing the thiazoline compound have been removed by standard isolation techniques.

The following examples illustrate specific aspects of the present invention. The examples are not intended to limit the scope of the invention in any respect and should not be so construed.

Example 1

4-Hydroxy-4-chloromethyl-2-(dimethylaminomethyl)thiazoline

A mixture of dimethylaminothioacetamide hydrochloride 54.0 g, 350 mmol), 1,3-dichloroacetone (52.0 g, 409 mmol) and sodium bicarbonate (64.0 g, 762 mmol) in 300 ml of toluene was stirred at 60° C. for 2 hours. The hot reaction solution was then cooled and salts which had precipitated during the reaction were removed by filtration. An equal volume of petroleum ether was then added to the filtrate and solids precipitated. These solids were recovered by filtration to afford 55.5 g of titled compound.

Twenty grams of the above material were further purified by dissolving them in 100 ml of a hot (60° C.) toluene solution. Any solids which did not dissolve were removed by filtration, and the resulting filtrate was slowly cooled to 10° C. while solids precipitated. These solids were recovered by filtration, washed with petroleum ether and then dried under nitrogen to afford 9.5 g of purified titled compound. This purified compound assayed by $^1$H and $^{13}$C NMR, using tetramethylsilane as internal standard, as follows:

$^1$H NMR (toluene, 300.13 mHz) d=2.03 (s, 6H); 3.03 (d, 2H); 3.05 (d, 2H); 3.10 (d, 2H); 3.22 (d, 2H) 3.52 (d, 2H); 3.67 (d, 2H).

$^{13}$C NMR (toluene, 75.47 mHz) d=39.09 ($CH_2$);45.40 ($CH_3$); 50.13 ($CH_2$); 61.14 ($CH_2$); 107.65 (C); 178.78 (C).

Example 2

2-(Dimethylaminomethyl)-4-exomethylenethiazoline epoxide

To a solution of 0.14 g (0.67 mmol) of the compound of Example 2 in 5 ml of toluene were added 0.015 g (0.65 mmol) of sodium metal. The resulting mixture was stirred under nitrogen for one hour at 20° C. and then filtered. The filtrate was assayed by $^1$H and $^{13}$C NMR, using tetramethylsilane as internal standard, which assay indicated that the filtrate contained titled compound. The assay results are as follows:

$^1$H NMR (toluene, 300.13 mHz) d=1.94 (s, 6H); 2.28 (d, 2H); 2.72 (d, 2H); 2.81 (d,2H); 3.06 (s, 2H); 3.12 (d, 2H).

$^{13}$C NMR (toluene, 75.47 mHz) d=33.51 ($CH_2$); 45.40 ($CH_3$); 53.54 ($CH_2$); 61.59 ($CH_2$); 87.06 (C); 179.24 (C).

Example 3

2-(Dimethylaminomethyl)-4-thiazolemethanol

To a 3 liter, three-necked, flask equipped with an agitator and condenser were added dimethylaminothioacetamide hydrochloride 270.0 g, 1.75 mol), sodium bicarbonate (320.0 g, 3.81 mol), 1,3-dichloroacetone (260.0 g, 2.05 mol) and toluene (1.5 liters). The resulting solution was heated to 40° C. and stirred at that temperature for one hour. After one hour the reaction solution was heated to 60° C. and stirred at that temperature for 3 hours. Solids which had precipitated during the reaction were then removed by filtration. Water (350 ml) was added to the hot (40° C.) filtrate and the resulting two-phase solution was cooled to approximately 15° C. Potassium hydroxide [300 ml of a 45% (weight percent) aqueous solution] was added to the cool two-phase solution at a rate such that the reaction mixture's temperature never exceeded 20° C. Once potassium hydroxide addition was completed, the reaction was completed as well. The reaction mixture was then allowed to warm to room temperature and the organic and aqueous layers were separated. The aqueous layer was extracted with four 750 ml portions of toluene. The toluene extracts and the above-mentioned organic layer were combined. The resulting solution was reduced to a dark oil by vacuum distillation (temperature 40° C.). This dark oil was then purified by high vacuum distillation (temperature 130°–140° C., pressure 1–2 mm Hg) to afford 232.4 g of a yellow oil which assayed according to the assay procedure described below as titled compound. The purity of this oil was greater than 99.0%.

The product produced above was characterized by an HPLC comparison with an authentic reference standard. The assay sample was prepared by placing 100 mg of product into a 50 ml volumetric flask, dissolving same with 10 ml of acetonitrile and then diluting to volume with an ion pairing solution (the ion pairing solution was prepared by dissolving 2 g of heptane sulfonic acid sodium salt in one liter of purified water, adding 1 ml of triethylamine and then adjusting the resulting solution's pH to 4.0 using glacial acetic acid). Ten milliliters of the diluted solution were transferred to a second 50 ml volumetric flask where they were then further dilute with an additional 10 ml of acetonitrile followed by dilution to volume with ion pairing solution. Once the assay sample was prepared 10 µl of the sample were injected onto a 25 cm Zorbax RX-C8 column. The detector had a wavelength of 254 nm, the column flow rate was 1.5 ml/min and the column temperature was ambient.

Example 4

2-(Dimethylaminomethyl)-4-thiazolemethanol

To a 100 ml, three-necked, flask equipped with an agitator and a condensor were added 3.0 g (0.014 mol) of 4-hydroxy-4-chloromethyl-2-dimethylaminomethyl)thiazoline (prepared as in Example 1), 45 ml of methanol and 4 ml of water. Potassium hydroxide [1.8 ml of a 45% (weight percent) aqueous solution] was added dropwise to the reaction solution at a rate such that the reaction temperature was maintained at room temperature. Once potassium hydroxide addition was completed, the reaction mixture was stirred at room temperature for an additional hour. A 1 ml sample of the reaction mixture was then removed from the flask, placed into a 50 ml volumetric flask and then diluted to volume with a 4:1 (v:v) acetonrile/water solution. One milliliter of the diluted sample solution was then placed in a 25 ml volumetric flask and further diluted to volume with a 4:1 (v:v) acetonitrile/water solution. Ten microliters of this solution were then assayed using the HPLC assay technique described in Example 3. Such HPLC assay indicated that 85.5% of the thiazoline substrate had converted to the desired titled product.

Example 5

2-(Dimethylaminomethyl)-4-thiazolemethanol

To a 100 ml, three-necked, flask equipped with an agitator and condensor were added 3.0 g (0.014 mol) of 4-hydroxy-4-chloromethyl-2-(dimethylaminomethyl) thiazoline (prepared as in Example 1), 47 ml of toluene, 1 ml of water and 0.79 g (0.014 mol) of solid potassium hydroxide. The resulting solution was stirred at room temperature for 45 minutes. A 1 µl sample of the reaction mixture was then removed from the flask and diluted according to the procedure described in Example 4. The HPLC assay set forth in Example 3 indicated that 72.6% of the thiazoline substrate had converted to the desired titled product.

Example 6

2-(Dimethylaminomethyl)-4-thiazolemethanol

The process of Example 5 was repeated using 0.56 g (0.014 mol) of solid sodium hydroxide in place of solid potassium hydroxide. The HPLC assay set forth in Example 3 indicated that 87.6% of the thiazoline substrate had converted to the desired titled product.

Example 7

2-(Dimethylaminomethyl) -4-thiazolemethanol

The process of Example 5 was repeated using 3.0 g (0.014 mol) of 4-hydroxy-4-chloromethyl-2-(dimethylaminomethyl)thiazoline (prepared as in Example 1), 48 ml of methanol and 0.98 g (0.014 mol) of potassium methoxide. The HPLC assay set forth in Example 3 indicated that 70.1% of the thiazoline substrate had converted to the desired titled product.

Example 8

2-(Dimethylaminomethyl)-4-thiazolemethanol

The process of Example 5 was repeated using 5.0 g (0.24 mol) of 4-hydroxy-4-chloromethyl-2-(dimethylaminomethyl)thiazoline, 25 ml of t-butylalcohol and 2.69 g (0.024 mol) of potassium t-butoxide. The HPLC assay set forth in Example 3 indicated that 90% of the thiazoline substrate had converted to the desired titled product.

Example 9

2-(Dimethylaminomethyl)-4-thiazolemethanol

To a 100 ml, three-necked, flask equipped with an agitator and a condensor were added 5.0 g (0.024 mol) of 4-hydroxy-4-chloromethyl-2-(dimethylaminomethyl)thiazoline, 25 ml of toluene and 1.3 g (0.024 mol) of sodium methoxide. The resulting solution was stirred at room temperature for one hour and then volatiles were removed under reduced pressure to provide an oil. This oil was then purified by high vacuum distillation (temperature 123°–128° C., pressure 1–2 mm Hg) to afford 1.74 g of a dark yellow oil which assayed by the HPLC assay described in Example 3 as titled compound.

Example 10

2-(Dimethylaminomethyl)-4-thiazolemethanol

To a 100 ml, three-necked, flask equipped with an agitator and a condensor were added 3.0 g (0.014 mol) of 4-hydroxy-4-chloromethyl-2-(dimethylaminomethyl)thiazoline and 45 ml of methanol. Sodium methoxide (0.78 g, 0.014 mol) was then dissolved in 15 ml of methanol and the resulting solution was added dropwise to the 100 ml flask at a rate such that the temperature of the flask's contents was maintained at room temperature. Once sodium methoxide addition was complete, the reaction mixture was stirred at room temperature for an additional two hours. Salts which had formed in the reaction was then removed by filtration, after which volatiles were removed under reduced pressure to provide an oil. This oil was purified by adding it to toluene, filtering off any undissolved material and then removing the toluene under reduced pressure to provide 1.99 g of an oil. This oil assayed by the HPLC assay described in Example 3 as titled compound.

Example 11

2-(Dimethylaminomethyl)-4-thiazolemethanol

To a 100 ml, three necked, flask equipped with an agitator and a condensor were added 3.0 g (0.014 mol) of 2-hydroxy-2-chloromethyl-2-(dimethylaminomethyl)thiazoline (prepared as in Example 1), 50 ml of toluene and 0.95 g (0.014 mol) of sodium ethoxide. The resulting solution was stirred at room temperature for 30 minutes. A 1 ml sample of the reaction mixture was then removed from the flask and diluted according to the procedure described in Example 4. The HPLC assay set forth in Example 3 indicated that 6.6% of the thiazoline substrate had converted to the desired titled compound.

Example 12

2-(Dimethylaminomethyl)-4-thiazolemethanol

To a 100 ml, three-necked, flask equipped with an agitator and a condensor were added 3.0 g (0.014 mol) of 2-hydroxy-2-chloromethyl-2-(dimethylaminomethyl)thiazoline (prepared as in Example 1), 50 ml of toluene and 0.34 g (0.014 mol) of sodium hydride. The resulting solution was stirred at room temperature for 4 hours. A 1 ml sample of the reaction mixture was then removed from the flask and diluted according to the procedure described in Example 4. The HPLC assay set forth in Example 3 indicated that 66.8% of the thiazoline substrate had converted to the desired titled compound.

The following examples illustrate the conversion of the 2-(aminomethyl)-4-thiazolemethanol compound produced by the process of the present invention into nizatidine.

Example 13

[2-(Dimethylaminomethyl)-4-thiazolylmethylthio]ethylamine

Fifty grams (0.291 mol) of the compound of Example 3 were placed in a 1 liter, three-necked, flask. To the flask was added a solution of 38.13 g (0.337 mol) of 2-aminoethanethiol hydrochloride dissolved in 73 ml of a 37% (weight %) aqueous hydrochloric acid solution. Once such solution was added, the reaction mixture was heated to reflux and stirred at that temperature for 15 hours. After 15 hours the reaction mixture was cooled to 95° C. and 142 ml of water were added. Cooling then continued until the solution temperature was approximately 15° C. Potassium hydroxide (132 ml of a 45% by weight aqueous potassium hydroxide solution) was then added in order to neutralize any unreacted acid. The resulting basic solution was extracted several times with toluene. These extracts were combined and then reduced in volume to provide 160.4 g of a toluene solution containing titled compound. This solution assayed as containing 58.8 g of titled compound in the gas chromatography assay described below. This same assay indicated that the toluene solution contained 6.7 g of impurities.

The solution produced above was characterized by gas chromatographic comparison with an authentic reference standard. The assay sample was prepared by placing 500 mg of solution into a 50 ml volumetric flask and then diluting to volume with methanol. The resulting solution was then transferred to a 100 ml volumetric flask and then diluted to volume with a 6 mg/ml undecane/methanol solution. Once the assay sample was prepared 2 µl of the sample were injected onto a 6 foot ×2 mm ID glass coil packed with 5% Carbowax 20M on 100/120 mesh chromatography GAW DMCS column. The injector, detector and oven temperatures utilized were 250° C., 250° C. and 75° C., respectively.

Example 14

N-[2-[[[2-[(Dimethylamino)methyl]-4-thiazolyl]methyl]thio]ethyl-N'-methyl-2-nitro-1,1-ethenediamine The toluene solution generated in Example 13 [99.6 g of solution; 50.0 g (0.216 mol) of the amine compound] was extracted three times with a 0.3% (weight %) sodium chloride solution. The aqueous extracts were combined in a 1 liter flask and then concentrated under reduced pressure to provide a solution weighing approximately 127 g. This solution was cooled to room temperature and 34.53 g (0.233 mol) of N-methyl-1-methylthio-2-nitroethyleneamine were added. The resulting solution was stirred at room temperature for 16 hours. After 16 hours acetone (500 ml) and activated carbon (1.8 g) were added to the thick, tacky, reaction mixture. The resulting suspension was heated to reflux, held at that temperature for 30 minutes, and then filtered, while hot. The collected solids were washed with 20 ml of hot acetone. The filtrate and acetone wash were combined, seeded with authentic titled compound and then allowed to cool to room temperature over a 1 hour period while solids precipitated. The resulting suspension was stirred at room temperature for 1 hour, cooled to 0° C. and stirred at that temperature for 30 minutes and then cooled to −10° C., The suspension was stirred at −10° C. for 4 hours and then filtered. The solids collected were washed with cold acetone (375 ml), air dried for 30 minutes and then vacuum dried at 60° C. for 18 hours to provide 63.4 g of titled compound. m.p. 130°–132° C. The HPLC assay described on pages 447 and 448 of Pharmacopeial Forum (May–June 1990) indicated that the titled compound was 99.4% pure on a solvent free basis.

The process of the present invention provides a method for synthesizing Nizatidine, other related compounds and key intermediates thereto, which is eminently suitable for use on a production scale. The substrates required by the present process are, in general, relatively inexpensive. The process steps required in order to synthesize Nizatidine and related compounds can all, generally, be accomplished in high yield while generating a minimum amount of impurities. Furthermore, what impurities are generated by the process for preparing Nizatidine and related compounds detailed herein are easily removed at several stages in the process, thereby obviating the need to remove such impurities once the final, pharmaceutically active, product has been prepared. As such, the present process is believed to provide a highly efficient and economical method for synthesizing pharmaceutically active anti-ulcer agents.

I claim:

1. A process for preparing a 2-(aminomethyl)-4-thiazolemethanol having the formula

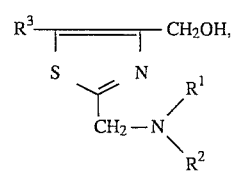

wherein

R$^1$ is hydrogen, methyl, ethyl, benzyl or benzoyl; R$^2$ is methyl or ethyl; or R$^1$ and R$^2$, taken together with the nitrogen atom to which they are attached, form a pyrrolidine, piperidine or morpholine ring; and R$^3$ is hydrogen or methyl;

which comprises reacting a 4-hydroxy-4-chloromethyl-2-(aminomethyl)thiazoline of the formula

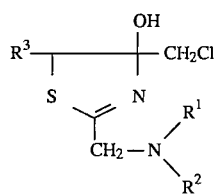

wherein $R^1$, $R^2$ and $R^3$ are as defined above, with an alkali metal base in an inert solvent selected from the group consisting of alcohol solvents and aromatic solvents.

2. A process of claim 1 wherein the base employed is potassium hydroxide.

3. A process of claim 2 wherein the inert solvent employed is methanol.

4. A process of claim 3 wherein $R^1$ and $R^2$ are both methyl and $R^3$ is hydrogen.

5. A process of claim 2 wherein the inert solvent employed is toluene.

6. A process of claim 5 wherein $R^1$ and $R^2$ are both methyl and $R^3$ is hydrogen.

7. A process of claim 1 wherein the inert solvent employed is methanol.

8. A process of claim 7 wherein $R^1$ and $R^2$ are both methyl and $R^3$ is hydrogen.

9. A process of claim 1 wherein the inert solvent employed is toluene.

10. A process of claim 9 wherein $R^1$ and $R^2$ are both methyl and $R^3$ is hydrogen.

11. A process of claim 1 wherein $R^1$ and $R^2$ are both methyl and $R^3$ is hydrogen.

12. A process of claim 11 wherein the base employed is potassium hydroxide.

* * * * *